(12) United States Patent
Chalvignac et al.

(10) Patent No.: US 8,915,247 B2
(45) Date of Patent: Dec. 23, 2014

(54) GAS SUPPLY UNIT FOR A RESPIRATORY SYSTEM

(75) Inventors: Philippe Auguste Chalvignac, Hunters Hill (AU); Jean-Philippe Mercier, Brie Comte Robert (FR)

(73) Assignee: ResMed Paris (FR)

(*) Notice: Subject to any disclaimer, the term of this patent is extended or adjusted under 35 U.S.C. 154(b) by 1302 days.

(21) Appl. No.: 12/527,838

(22) PCT Filed: Feb. 20, 2007

(86) PCT No.: PCT/IB2007/051453
§ 371 (c)(1),
(2), (4) Date: Jan. 4, 2010

(87) PCT Pub. No.: WO2008/102216
PCT Pub. Date: Aug. 28, 2008

(65) Prior Publication Data
US 2010/0139657 A1    Jun. 10, 2010

(51) Int. Cl.
*A61M 11/00* (2006.01)
*A61M 16/00* (2006.01)
*A61M 16/10* (2006.01)

(52) U.S. Cl.
CPC ....... *A61M 16/0057* (2013.01); *A61M 16/0066* (2013.01); *A61M 2016/0027* (2013.01); *A61M 2016/0039* (2013.01); *A61M 2016/1025* (2013.01); *A61M 2205/12* (2013.01); *A61M 2205/125* (2013.01); *A61M 2205/128* (2013.01); *A61M 2205/8206* (2013.01)
USPC ................................. 128/204.18; 128/205.24

(58) Field of Classification Search
USPC ............ 128/204.18, 204.19, 204.21, 204.22, 128/204.23, 204.26, 204.27, 205.11, 128/205.12, 205.24, 202.27
See application file for complete search history.

(56) References Cited

U.S. PATENT DOCUMENTS

| | | | |
|---|---|---|---|
| 4,957,107 A | 9/1990 | Sipin | |
| 5,211,171 A | 5/1993 | Choromokos | |
| 6,202,642 B1 | 3/2001 | McKinnon et al. | |
| 6,302,105 B1 | 10/2001 | Wickham et al. | |
| 7,121,276 B2 * | 10/2006 | Jagger et al. | 128/204.18 |
| 7,677,246 B2 * | 3/2010 | Kepler et al. | 128/204.18 |

FOREIGN PATENT DOCUMENTS

| | | |
|---|---|---|
| DE | 100 21 783 A1 | 11/2000 |
| JP | 05154200 A | 6/1993 |
| WO | 2006045602 A1 | 5/2006 |
| WO | WO-2006/117379 A2 | 11/2006 |

* cited by examiner

*Primary Examiner* — Laura Bouchelle
(74) *Attorney, Agent, or Firm* — Lerner, David, Littenberg, Krumholz & Mentlik, LLP

(57) ABSTRACT

The invention relates to a gas supply unit (1) for supplying pressurized gas to a patient (8), wherein it comprises:—A pneumatic housing (10) for supplying a flow of gas to the patient (P), • A control housing (20) for controlling the flow of gas to be supplied to the patient (P), and A power supply housing (30) for supplying power to the unit (1), wherein the three housings (10,20,30) are distinct from one another and are designed for being removably coupled together to form a single unit (1). It further relates to a respiratory System for supplying a patient (P) with pressurized gas, the System comprising such a gas supply unit (1).

21 Claims, 3 Drawing Sheets

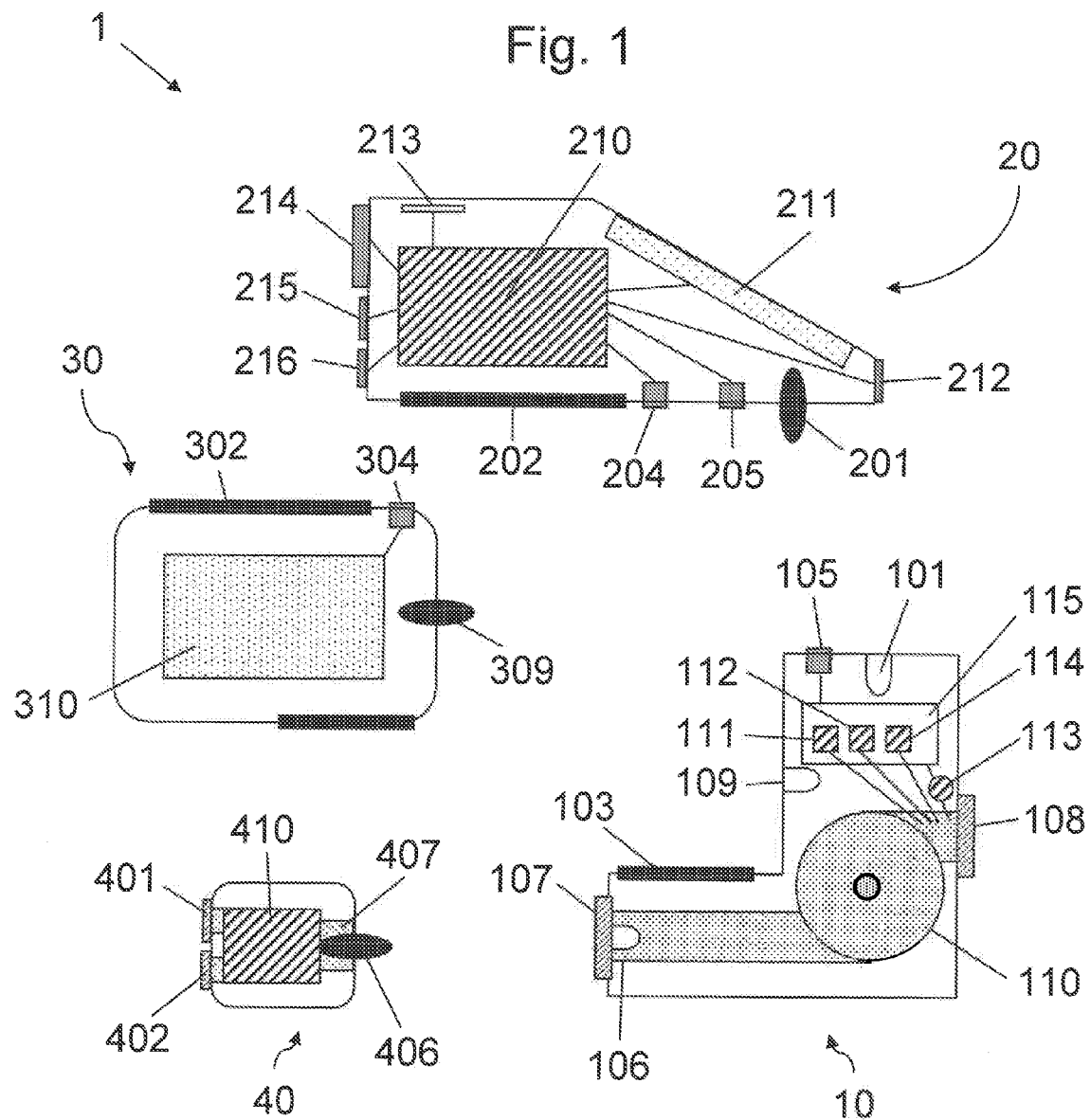

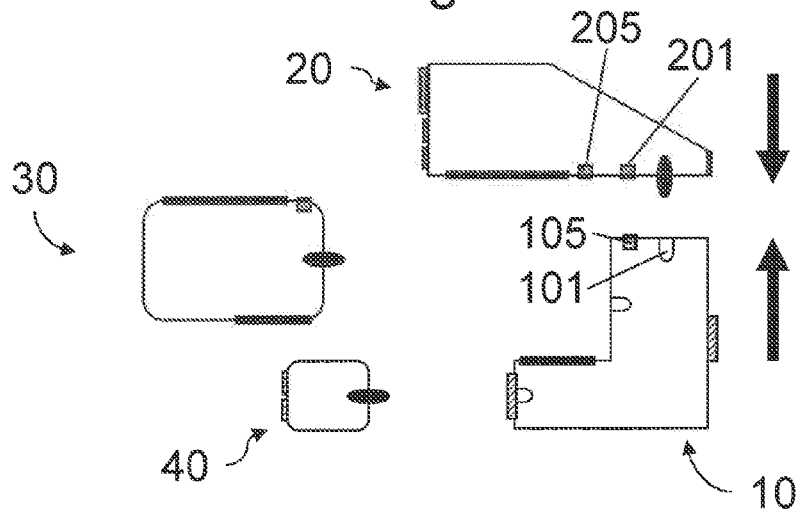
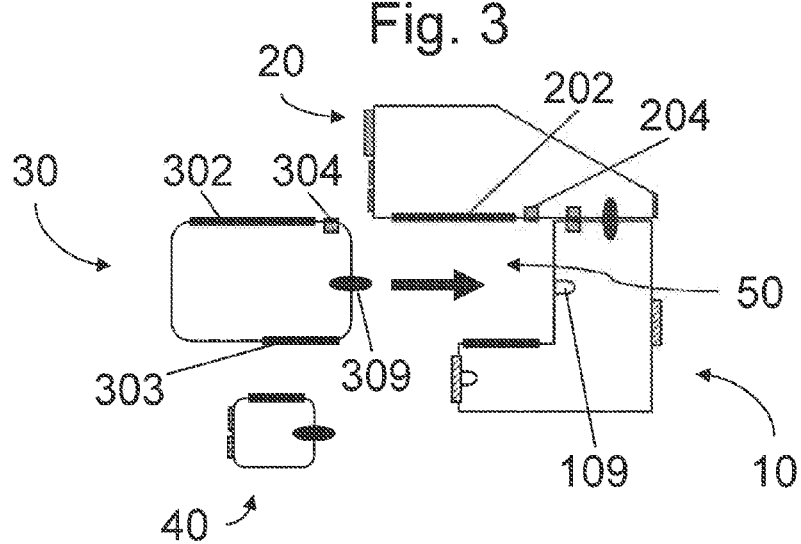
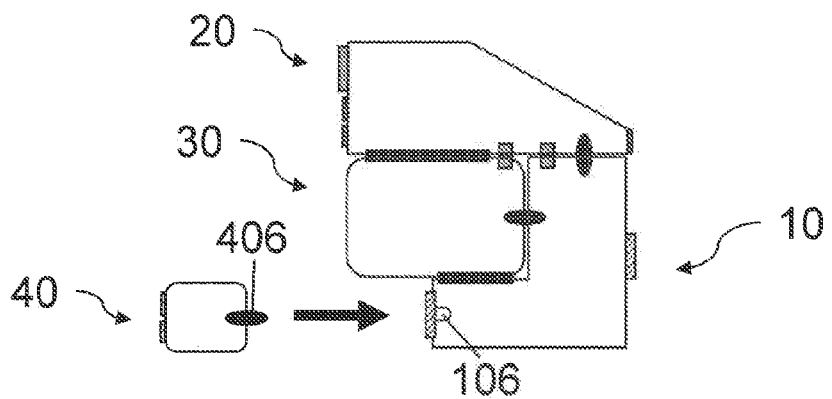

GAS SUPPLY UNIT FOR A RESPIRATORY SYSTEM

FIELD OF THE INVENTION

The present invention relates to a respiratory system for a patient. It more precisely relates to a gas supply unit for feeding a patient with breathable gas, to be used for treatment of any disorder that requires assisted and/or controlled ventilation of the patient.

TECHNICAL BACKGROUND

Ventilation of a patient involves the delivery of a breathable gas (typically ambient air to which a complementary gas such as oxygen can be added) pressurised above atmospheric pressure to a patient via a conduit, and a mask or tracheotomy tube.

There are more and more troubles that require assisted and/or controlled ventilation of the patient. It is namely common to use breathing assistance devices for diseases where mechanical ventilation is needed, for example in neuromuscular disease where volume controlled ventilation is required. These devices may also be used for other respiratory diseases or disorders, such as for the continuous positive airway pressure (CPAP) treatment of obstructive sleep apnea.

For either application of assisted and/or controlled ventilation, the pressure of the gas delivered to patients can be constant level, bi-level (in synchronism with patient breathing) or auto-adjusting in level. Further, some troubles require feeding the patient with a controlled volume of breathable gas, such as for neuromuscular patients. Throughout this specification reference to gas supply unit is intended to incorporate a reference to any one of, or combinations of, these forms of pressurised gas supply.

A disadvantage of existing gas supply units is the danger of biological contamination and disease/virus/bacteria transfer. More particularly, there can be a significant reverse flow during heavy expiration and/or coughing and biological material exhaled by a patient can be deposited in the gas supply unit. In this case, a patient continually using the same machine can be re-infected by a prior condition, or the deposited biological material may be transferred to another patient who uses the same machine.

A gas supply unit generally comprises a closed outer casing surrounding internal components. Components inside, and constituting part of, the gas flow path include for instance the gas inlet, inlet filter, impeller, and gas outlet. Components outside the gas flow path include control electronics, power regulators and motor. As a result, such gas supply units have a gas flow path that is extremely difficult to clean/sterilise without the time consuming dismantling and removal of all the "gas flow path" components. Further, without disassembly, common sterilisation procedures such as autoclaving will damage the circuit boards and other electrical components.

As a consequence, gas supply units have been developed to overcome this problem in separating the components inside the gas flow path from the outside components. In the United States Patent published on Oct. 16, 2001 under the reference U.S. Pat. No. 6,302,105, Wickham et al. have for example proposed a gas supply unit with a main housing for the components outside the gas flow and a sub-housing for the components inside the gas flow. However, for complete independence of the sub-housing from the main housing, coupling of the inside and outside components is relatively complex and increases the size of the gas supply unit. This is especially true for gas supply units enabling treatment of serious respiratory troubles. Such increase in the size of the unit is disadvantageous in view of the preference for miniaturization of breathing assistance devices for improving the patient's comfort. Furthermore such devices do not enable feeding a patient with a controlled volume of breathable gas which may be required for some specific treatment.

Therefore, it is an object of the present invention to provide a gas supply unit that substantially overcomes or at least ameliorate one or more of the above deficiencies.

SUMMARY OF THE INVENTION

A first aspect of the invention is to provide a compact gas supply unit adapted for assisted and/or controlled ventilation with easy to clean components inside the gas flow.

A further aspect of the invention is to provide a gas supply unit which is safe for the user.

One form of the invention comprises a gas supply unit which may be adapted for any respiratory treatment of a patient, in particular for patients with serious respiratory troubles.

In one form the invention proposes a respiratory system as defined in claim 1.

In a preferred embodiment, the invention concerns a gas supply unit for supplying pressurised gas to a patient, characterised in that it comprises:
- A pneumatic housing for supplying a flow of gas to the patient,
- A control housing for controlling the flow of gas to be supplied to the patient, and
- A power supply housing for supplying power to the unit, wherein the three housings are distinct from one another and are designed for being removably coupled together to form a single unit.

Preferable but not limited aspects of such a gas supply unit are the following:
- the housings are removably coupled together by way of couplings that may comprise clips;
- the power supply housing comprises fasteners designed for preventing the pneumatic housing and the control housing from being uncoupled from one another as long as the power supply housing is coupled to the pneumatic housing and the control housing;
- the fasteners comprise longitudinal grooves provided on the power supply housing for cooperation with longitudinal ridges provided on both the pneumatic housing and the control housing;
- the pneumatic housing is provided with apertures for receiving gas to be supplied to the patient, and comprises a filter for filtering the gas before supplying to the patient;
- the unit further comprises a distinct filter housing for filtering the gas to be supplied to the patient, wherein the filter housing is designed for being removably coupled to the pneumatic housing; such filter housing encloses a filter and is provided with apertures for receiving gas to be supplied to the patient, and wherein the pneumatic housing and the filter housing are in fluid communication for transmission of the filtered gas from the filter housing to the pneumatic housing;
- the power supply housing and the control housing comprise cooperative connectors for electrically connecting the power supply means of the power supply housing with the controller of the control housing, when the housings are coupled together;
- the control housing and the pneumatic housing comprise cooperative connectors for electrically connecting the controller of the control housing with the pneumatic supply device of the pneumatic housing when the housings are coupled together;

the controller of the control housing comprises a data processor for controlling the flow of gas to be supplied to the patient;

the data processor integrates data characteristics of the gas flow in order to adequately control the flow of gas;

the controller of the control housing comprise a user interface for a user to manage operation of the unit, and wherein the data processor integrates data from the user interface in order to adequately control the flow of gas.

the data processor are adapted for controlling the pneumatic supply device of the pneumatic housing for supplying a controlled flow of gas;

the pneumatic supply device of the pneumatic housing comprises a turbine for compressing the gas arriving in the pneumatic housing and for propelling the pressurised gas to the patient;

the pneumatic supply device of the pneumatic housing comprise a printed circuit board connected with sensors for sensing characteristics of the flow of gas within the pneumatic housing, the printed circuit board being further connected with the controller of the control housing for transmission of data characteristics of the flow of gas;

the sensors comprise a gas flow sensor, a pressure sensor, a temperature sensor, and/or an oxygen sensor for sensing the amount of oxygen within the flow of gas;

the pneumatic housing comprises a gas outlet for being connected to gas conduit, the gas conduit being adapted for conveying the pressurised gas to the patient.

According to a further aspect of the invention, there is proposed a respiratory system for feeding a patient breathing in successive cycles with pressurised gas, each cycle being defined by at least an inspiration phase and at least an expiration phase, characterised in that the respiratory system comprises a gas supply unit according to any one of the preceding claims, a gas conduit for conveying the pressurised gas from the gas supply unit to the patient through an expiratory valve, the expiratory valve being adapted for management of the gas flow depending on the phase of the cycle.

This respiratory system may further comprise a connector for electrically connecting the controller of the control housing with the expiratory valve, and through which the controller controls the expiratory valve in order to supply a controlled flow of gas to the patient from the expiratory valve.

BRIEF DESCRIPTION OF THE DRAWINGS

Other characteristics and advantages of the invention will become clear from the following description which is only given for illustrative purposes and is in no way limitative and should be read with reference to the attached drawings on which:

FIG. 1 schematically illustrates the structure of a gas supply unit according to an embodiment of the invention;

FIGS. 2 to 4 schematically illustrate the coupling of the different housings forming the gas supply unit of FIG. 1;

DETAILED DESCRIPTION OF THE DRAWINGS

Structure of the Gas Supply Unit

Figure 5:
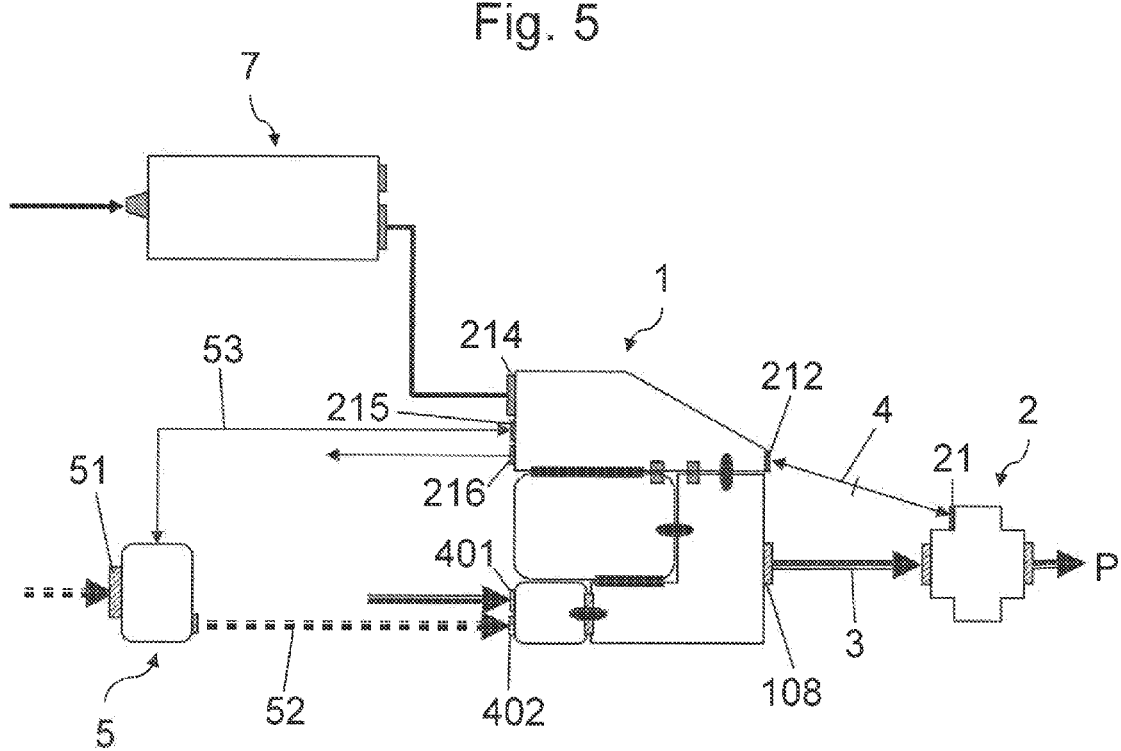
FIG. 5 schematically illustrates a respiratory system incorporating the gas supply unit of FIG. 1.

It has first to be noted that FIGS. 1 to 5 are schematic illustration and that they only intend to explain the structure of the gas supply unit and coupling of the different housings that form this gas supply unit. In particular, representation of electrical connections is not indicative of the number of wires that may be used for these connections.

FIG. 1 schematically illustrates a gas supply unit 1 that comprises three main housings (10, 20, 30) that allows the gas supply unit 1 to supply a controlled flow pressurised gas to a patient P.

The three housings (10, 20, 30) are namely distinct casings that are designed to be removably coupled together, each of these housings (10, 20, 30) enclosing specific components for the gas supply unit 1 to work. As described in detail hereinafter, the gas supply unit 1 namely comprises a pneumatic housing 10 which encloses pneumatic supply device for supplying a flow of gas to the patient P, control housing 20 for controlling the flow of gas to be supplied to the patient P, and a power supply housing 30 for supplying power to the gas supply unit.

The pneumatic housing 10 is designed to enclose a pneumatic supply device for supplying a flow of gas to a patient. Such a pneumatic supply device may basically comprise a turbine 110, preferably of a small size, that is adapted for compressing the gas arriving in the pneumatic housing 10 through a gas inlet 107, and for propelling such pressurised gas to the patient P through a gas outlet 108.

The pneumatic supply device enclosed in the pneumatic housing 10 may also comprise sensors (111, 112, 113, 114) for sensing the flow of gas through the pneumatic housing 10. These sensors are preferably arranged to sense the flow of gas to be supplied by the gas supply unit 1, that is at the gas outlet 108. Thus, there is preferably provided a gas flow sensor 111, such as a hot wire sensor, and a pressure sensor 112. Other sensors may also be provided such as an oxygen sensor 113 for sensing the amount of oxygen within the flow of pressurised gas, and/or a temperature sensor 114.

Preferably, the sensors are connected to a printed circuit board 115 as illustrated in FIG. 1. Such printed circuit board 115 aims at gathering the data collected from the different sensors (111, 112, 113, 114). As it will be explained in more detail below, this allows having a simple electrical connection between the pneumatic housing 10 and the controlling housing 20.

As it will also be explained in more detail below, the pneumatic housing 10 is provided with coupling 101, such as a clip 101, designed to cooperate with coupling 201 provided on the control housing 20 to removably couple both housings. The pneumatic housing 10 also comprises fastener 103 adapted to cooperate with fastener 303 provided on the power supply housing 30 for preventing the pneumatic housing 10 and the control housing 20 from being uncoupled from one another as long as the power supply housing 30 is coupled to the pneumatic housing 10 and the control housing 20. Such coupling 101 and fastener 103 may be directly moulded with the pneumatic housing 10, or simply provided thereon.

The gas which has to be compressed by the turbine enters the pneumatic housing 10 through the gas inlet 107. The pneumatic housing 10 may be provided with a filter for filtering the entering gas and supplying a more purified gas to the patient P. Such filter may be enclosed within the pneumatic housing 10 between the gas inlet 107 and the turbine 110.

According to another preferred embodiment, the gas supply device 1 comprises a distinct filter housing 40 enclosing the filter 410. This filter housing 40 is designed to be coupled in fluid communication with the pneumatic housing 10 at the gas inlet 107. The filter housing 40 has therefore a gas outlet 407 adapted to be connected to the gas inlet 107 of the pneumatic housing 10. The filter housing further comprises coupling 406, such as a clip 406, designed to cooperate with coupling 106 provided at the gas inlet 107 of the pneumatic housing 10. Here again, the coupling 406 (respectively 106) may be directly moulded with the filter housing 40 (respectively the pneumatic housing 10), or simply provided thereon.

Further, the filter housing 40 comprises at least two gas inlets. The first gas inlet 401 is an air inlet provided such that air from the ambient atmosphere enters the filter housing 40 and passes through the filter 410. Another gas inlet 402 is provided on the filter housing 40 for connection with an external gas source, such as a source of oxygen. Such gas also passes through the filter 410, where it is mixed with air from ambient atmosphere, such that a filtered gas mixture enters the pneumatic housing 10. It may also be desirable to provide the filter housing 40 with more than two gas inlets, in case it is needed to mix several gases with ambient air for example.

The second main housing of the gas supply unit 1 is the control housing 20 which is designed to receive a controller for controlling the flow of gas to be supplied to the patient P. This controller may directly control the turbine 110 which then would regulate the flow of gas supplied by the gas supply unit 1. It is also possible that the controller is adapted to control an active expiratory valve disposed in a duct between the gas supply unit 1 and the patient P, this expiratory valve being adapted to regulate the flow of gas in response to the controller. According to another embodiment, the controller controls both the turbine 110 and an active expiratory valve to control the gas flow to be supplied to the patient.

The controller comprises a data processor 210, such as a central processing unit (CPU), that integrates several data and adequately controls the gas flow to be supplied to the patient P.

Indeed, the data processor 210 is first adapted to integrate data received from the sensors (111, 112, 113, 114), in order to characterize the flow of gas at the gas outlet 108 (pressure, flow rate, amount of oxygen, temperature, etc.). Each sensor may be directly connected to the data processor 210 but preferably there is a simple electrical connection between the pneumatic housing 10 and the control housing 20. To this end, as illustrated in FIG. 1, the different sensors (111, 112, 113, 114) are connected to a printed circuit board 111 which is electrically connected with the data processor 210 of the control housing 20, by way of cooperative connectors (105, 205) provided on the pneumatic housing 10 and the control housing 20 respectively. These connectors (105, 205) may for example be cooperative plugs that are connected together when the pneumatic housing 10 and the control housing 20 are coupled together.

The data processor 210 is further adapted to integrate data received from a user interface 211. Indeed, the controller comprises a user interface 211, so that a user may easily manage operation of the gas supply unit 1. Such user interface 211 may for example comprise a keyboard and a display that allow a user to specify the type of gas mixture the patient need, at which flow rate and pressure the gas has to be supplied to the patient, and any other parameters that may be of interest for answering the needs of the patient with regard to ventilation.

According to another embodiment, the control housing 20 further comprises a data card receiver 213 for receiving a memory card that contains data relative to the patient that could be used for adequately control the flow of gas to be supplied to the patient. To this end, the data card receiver 213 is electrically connected to the data processor 210 which is adapted to integrate the data for controlling the supplied gas flow.

As explained above, for controlling the flow of gas supplied to the patient, the controller may control the turbine, an active expiratory valve or both of them. In the embodiment illustrated in FIG. 1, the data processor 210 is adapted to control an expiratory valve through an electrical connector 212 provided on the control housing 10. This electrical connector 212 may be a plug to which is connected one or more wires for electrically connecting the data processor 210 with the expiratory valve.

As already stated above and as it will be explained in more detail below, the control housing 20 is provided with coupling 201, such as a clip 201, designed to cooperate with coupling 101 provided on the pneumatic housing 10 to removably couple both housings. Further, the control housing 20 comprises fastener 202 adapted to cooperate with fastener 302 provided on the power supply housing 30 for preventing the pneumatic housing 10 and the control housing 20 from being uncoupled from one another as long as the power supply housing 30 is coupled to the pneumatic housing 10 and the control housing 20. Such coupling 201 and connector 202 may be directly moulded with the control housing 20, or simply provided thereon.

The control housing 20 is also provided with an electrical connector 204 arranged for being connected to a corresponding connector 304 provided on the power supply housing 30. These connectors (204, 304) may for instance be cooperative plugs that are connected together when the power supply unit is coupled to the control housing 20. Such electrical connection allows supply of power to the data processor 210 which feeds every component requiring power to work, such as the turbine which is power fed through the connector (105, 205) and the printed circuit board 115.

Finally, as it will be explained in more detail below, the control housing 20 may be provided with other electrical connectors (214, 215, 216) for connection of the data processor 210 to external devices, such as an external power supply source.

The third main housing 30 is a power supply housing 30 that is designed for enclosing a power supply unit 310. The power supply unit may be any kind of battery, such as a Li ion battery for instance.

It is namely necessary to supply power to the gas supply unit 1, and more particularly to components that require power for operation, such as the data processor 210, the user interface 211, the turbine 110, etc.

To this end the power supply housing 30 is provided with connector 304 that enable, as stated above, the supply of power to the controller of the control housing 20, when the power supply housing 30 is coupled with the control housing 20.

As also stated above, the power supply housing 30 is provided with fasteners 302 and 303 that are adapted to cooperate with the fasteners 202 and 103 of the control housing 20 and the pneumatic housing 10 respectively. These fasteners are designed and arranged in order to prevent the pneumatic housing 10 and the control housing 20 from being uncoupled from one another as long as the power supply housing 30 is coupled to the pneumatic housing 10 and the control housing 20. Such fasteners 302 and 303 may be directly moulded with the power supply housing 30, or simply provided thereon. Coupling 309, such as a clip, may also be moulded with or provided on the power supply housing 30. Such couplings 309 are designed to cooperate with couplings 109 provided on the pneumatic housing 10 so that both housings may be removably coupled together. According to another embodiment, the coupling 309 is designed to cooperate with a coupling provided on the control housing 20.

Coupling of the Housings of the Gas Supply Unit

FIGS. 2 to 4 schematically illustrate the coupling of the different housings (10, 20, 30, 40) forming the gas supply unit 1.

As illustrated in FIG. 2, the first step comprises assembling the pneumatic housing 10 and the control housing 20.

As explained above, the pneumatic housing 10 and the control housing 20 are respectively provided with couplings (101, 201) that enable easy and removable coupling of both housings. These couplings may for example consist in cooperative clips that hold the housings (10, 20) together when assembled.

Use of clips (101,201) for coupling these housings (10, 20) has the advantage of providing easy mounting and dismounting of the gas supply unit 1. For coupling the pneumatic housing 10 and the control housing 20, it is only necessary to bring each of the housings (10, 20) towards the other according to the arrows of FIG. 2 until the housings (10, 20) are clipped together. This design also provides simple disassembly of one of the housings from the other, via a simple unclipping. As a consequence, no tools are required for such operation, which is very convenient for the user.

Further the clips (101, 201) may be designed to act as a guide for the coupling of the pneumatic housing 10 with the control housing 20. This eases connection of the connectors (105, 205) that are respectively provided on the pneumatic housing 10 and the control housing 20. Indeed, these connectors (105, 205) are aligned during coupling thanks to the guidance of the clips (101, 201).

For transportation, the gas supply unit 1 needs to be self-powered. To this end, after having coupled the pneumatic housing 10 and the control housing 20 together, it is necessary to connect the power supply housing 30 that comprises the power supply unit 310, such as a rechargeable battery.

As stated above, the power supply housing 30 is provided with fasteners 302 and 303 adapted to cooperate with fasteners 202 and 103 respectively provided on the control housing 20 and the pneumatic housing 10.

For example, the fasteners 302 and 303 of the power supply housing 30 comprise longitudinal grooves that are arranged for cooperating with longitudinal ridges provided on both the pneumatic housing 10 and the control housing 20. According to such an embodiment, the power supply housing 30 only requires insertion into a space 50 formed between the pneumatic housing 10 and the control housing 20 when coupled together. The arrow represented in FIG. 3 illustrates such an insertion.

The aim of the cooperative fasteners (103, 303, 202, 302) is to prevent the pneumatic housing 10 and the control housing 20 from being uncoupled from one another as long as the power supply housing 30 is coupled to the pneumatic housing 10 and the control housing 20. These cooperative fasteners (103, 303, 202, 302) are more precisely designed and arranged for preventing the pneumatic housing 10 and the control housing 20 from being uncoupled from one another as long as the power supply housing 30 is capable of supplying power to the control housing 20, i.e. as long as the connectors (204, 304) are connected together. When power is supplied by the power supply unit 310, electric signals or power is transmitted between components of the gas supply unit 1, and more particularly between the connectors (205, 105) that electrically connect the control housing 20 and the pneumatic housing 10. Without the fasteners (103, 303, 202, 302), the control housing 20 and the pneumatic housing 10 could be uncoupled at any time, including when electric signals or power is transmitted through the connectors (205, 105), which would create electric arcs between the control housing 20 and the pneumatic housing 10. Such electric arcs, which are dangerous for the user, are avoided in the gas supply unit 1 described in this document as the fasteners (103, 303, 202, 302) prevent such inopportune uncoupling of the control housing 20 from the pneumatic housing 10. Thus, safety of the patient is increased during operation of the gas supply unit 1.

Furthermore, guiding of the power supply housing 30 during its insertion would ease the assembling of the device, and allow precise connection of the connectors (204, 304) respectively provided on the control housing 20 and the power supply housing 30. Such guiding may be performed by any method. According to a preferred embodiment, this guiding is performed by cooperation of the fasteners (103, 303, 202, 302), which is for example the case when the fasteners 302 and 303 of the power supply housing 30 comprise longitudinal grooves that are arranged for cooperating with longitudinal ridges provided on both the pneumatic housing 10 and the control housing 20.

When fully inserted within the space 50 between the pneumatic housing 10 and the control housing 20, the clip 309 of the power supply housing 30 engages the corresponding clip 109 of the pneumatic housing 10. Such cooperation of the clips (309, 109) hold the power supply housing 30 assembled with the pneumatic housing 10.

As a consequence the three main housings (10, 20, 30) are held together by way of the different clips to form the desired gas supply unit 1. Such coupling simplifies assembling and disassembling of the gas supply unit 1. As no tools are required, assembly and disassembly of the unit may be done by anybody, anywhere, and very easily.

Furthermore, not only the gas supply unit 1 is modular, it is also perfectly safe for the user due to the fasteners provided on the different housings (10, 20, 30).

Consequently, each distinct housing and the different components it encloses may be treated separately. After use of the gas supply unit 1 by a patient P, the "polluted" housing enclosing components within the gas flow path, such as the pneumatic housing 30, may be removed and replaced by a clean, sterile or disinfected housing. Alternatively, the "polluted" housings may be removed, cleaned, sterilised or disinfected, and then reinstalled.

As it has been explained above, a filter may be used for filtering the gas passing through the pneumatic housing 10. To this end, the filter may be enclosed within the pneumatic housing 10 itself, or the filter 410 is located within a distinct filter housing 40.

FIG. 4 illustrates coupling of such a filter housing 40 with the corresponding pneumatic housing 10. This coupling can be made at any stage of the assembly of the gas supply unit 1, that is before having coupled the pneumatic housing 10 and the control housing 20 together, or after having coupled the pneumatic housing 10 and the control housing 20 together but before inserting the power supply housing 30, or after having coupled the three main housings (10, 20, 30) all together as illustrated in FIG. 4.

As mentioned previously, use of clips (106,406) for coupling the filter housing 40 with the pneumatic housing 10 has the advantage of providing easy mounting and dismounting with the gas supply unit 1. For coupling the filter housing 40 with the pneumatic housing 10, it is only necessary to bring the filter housing 40 towards the pneumatic housing 10 according to the arrow of FIG. 4 until the housings (10, 40) are clipped together. This also provides for simple disassembly of the filtering housing 40 from the pneumatic housing 10 as a simple unclipping is required. As a consequence, no tools are required for such operation which is very convenient for the user.

Operation of the Gas Supply Unit within the Respiratory System

As illustrated in FIG. 5, the gas supply unit 1 may be used in a respiratory system for feeding a patient P breathing in successive cycles with pressurised gas, each cycle being defined by at least an inspiration phase and at least an expiration phase.

To this end, the gas outlet 108 of the gas supply unit 1 is connected to gas conduit 3 that is connected to a patient P (via a mask or by tracheotomy tube for example) for providing pressurised gas to the patient P. Such a gas conduit 3 may comprise for example a single duct 3, with an expiratory valve 2 interposed.

The expiratory valve 2 is adapted for conveying the pressurised gas from the gas supply unit 1 to the patient P during inspiration phases. The gas rejected by the patient P during expiration phases has to be expulsed to the ambient air. In case of tracheotomy or when the mask is not adapted for rejection of the expiratory gas, the expiratory valve has also to be adapted for rejection of gas to ambient air during expiration phases. Such rejection of expiratory gas may also be done through leakage orifices provided on the mask.

The flow of gas that is supplied to the patient P may be controlled as explained above. Such control may be done by directly controlling the turbine 110, and/or by controlling the expiratory valve 2. The PCT application published on Nov. 9, 2006 under the reference WO2006/117379 describes some expiratory valves that would be adapted for such operation of the respiratory system, incorporated herein by reference in its entirety. In the case where the expiratory valve controls the gas flow to be supplied to the patient P, an electrical link 4 is provided between connector 212 provided on the control housing 20 of the gas supply unit 1 and connector 21 provided on the expiratory valve 2. Such connectors enable transfer of electric signals and/or power between the expiratory valve 2 and the gas supply unit 1. For instance, if sensors (such as pressure sensor or gas flow sensor) are provided within the expiratory valve 2, the collected data could be used by the data processor 210 to adapt control of the gas flow.

As stated above, the gas supply unit 1 comprises an air inlet 401 through which air from the ambient atmosphere enters the pneumatic housing 10. There is also provided at least a gas inlet 402 so that gas from an external gas source can enter the pneumatic housing 10.

The gas inlet 402 may comprise a standard connection to allow direct connection to an external gas source under high pressure. However, such a standard connection has a relatively large size which increases the volume of the gas supply unit 1. In this case, the gas supply unit may also require a gas regulator to be included in the pneumatic housing for regulating the pressure and flow of the external gas to be mixed with ambient air. Thus, the gas supply unit would be larger in size.

Another solution consists in using an external unit 5 adapted for being connected to an external gas source under high pressure, and which is also adapted for regulation of the pressure and flow of the external gas to be mixed with ambient air within the pneumatic housing 10. Such external unit is for example described in the PCT application published on Dec. 28, 2006 under the reference WO2006/136878, incorporated herein by reference in its entirety. The advantage of using such an external unit 5 is that it allows the gas supply unit 1 to be very compact, as it does not require any standard connector or gas regulator for regulation of the external gas. Indeed, if a particular gas needs to be mixed with ambient air before feeding the patient, the external unit 5 is connected to an external gas source under high pressure via a standard connector 51, and the gas regulator enclosed within the external unit 5 regulates the pressure and flow of the gas that will be supplied to the pneumatic housing 10. Therefore, the external gas is regulated such that a single duct 52 can be used to feed the pneumatic housing 20, and it is not necessary to provide the pneumatic housing 20 with a special connection 402 or any gas regulator. An electrical link 53 is also provided between connector 215 provided on the control housing 20 of the gas supply unit 1 and the external unit 5. Such connector enables transfer of electric signals and/or power between the external unit 5 and the gas supply unit 1. Electric signals can therefore be transmitted between the data processor 210 and the gas regulator of the external unit 5 in order to adequately regulate the external gas to be supplied to the pneumatic housing 20.

The gas supply unit may also be connected to an external power supply 7 through connector 214 connected to the data processor 210 of the control housing 20.

Such an external power supply 7 may be convenient for instance when the patient does not need to move and/or has to be assisted by the respiratory system for a long period of time.

Another advantage of such an external power supply 7 is that it may be used to recharge the rechargeable battery enclosed in the power supply housing 30. Therefore, it is not necessary to stop the gas supply unit for recharging the battery which is very convenient for patients that need continuous breathing assistance and may also need to move from one location to another.

Finally, connector 216 may be a wireless connection to a remote alarm that could be triggered to give an alert for signalling any problem relative to operation of the respiratory system, or for the patient to call emergencies.

The wireless connection 216 may also provide remote access to manage the operation of the respiratory system, for example by uploading operating data remotely. Such remote management would be very useful in preventing any contamination from the patients, especially in cases where the patient is contagious and should not be approached.

The wireless connection 216 could also be used for remotely monitoring operation of the respiratory system and ventilation of the patient, by using ventilation curves or any monitoring parameters.

The reader will have understood that many modifications may be made without going beyond the new information and the advantages described herein. Consequently, all modifications of this type shall be within the scope of the gas supply unit and breathing assistance device as defined in the attached claims.

The invention claimed is:

1. A gas supply unit for supplying pressurised gas to a patient comprising:
   a pneumatic housing including a pneumatic supply device for supplying a flow of gas to the patient,
   a control housing including a controller for controlling the flow of gas to be supplied to the patient, and
   a power supply housing for supplying power to the unit,
      wherein the three housings are distinct from one another and are designed for being removably coupled together to form a single unit and wherein at least two of the pneumatic housing, the control housing and the power supply housing include complementary couplings configured for coupling the two housings to each other when aligned together.

2. The unit of claim 1, wherein the housings are removably coupled together by way of couplings.

3. The unit of claim 2, wherein the couplings comprise clips.

4. The unit of claim 1, wherein the pneumatic housing is provided with apertures for receiving gas to be supplied to the patient, and comprises a filter for filtering the gas before supplying to the patient.

5. The unit of claim 1, further comprising a filter housing for filtering the gas to be supplied to the patient, wherein the filter housing is designed for being removably coupled to the pneumatic housing.

6. The unit of claim 5, wherein the filter housing is provided with apertures for receiving gas to be supplied to the patient, and wherein the pneumatic housing and the filter housing are in fluid communication for transmission of the filtered gas from the filter housing to the pneumatic housing.

7. The unit claim 1, wherein the power supply housing and the control housing comprise cooperative connectors for electrically connecting the power supply means of the power supply housing with the controller of the control housing, when the housings are coupled together.

8. The unit of claim 1, wherein the control housing and the pneumatic housing comprise cooperative connectors for electrically connecting the controller of the control housing with the pneumatic supply device of the pneumatic housing when the housings are coupled together.

9. The unit of claim 1, wherein the controller of the control housing comprises a data processor for controlling the flow of gas to be supplied to the patient.

10. The unit of claim 9, wherein the data processor integrates data characteristics of the gas flow in order to adequately control the flow of gas.

11. The unit of claim 9, wherein the controller of the control housing comprise a user interface for a user to manage operation of the unit, and wherein the data processor integrates data from the user interface in order to adequately control the flow of gas.

12. The unit of claim 9, wherein the data processor are adapted for controlling the pneumatic supply device of the pneumatic housing for supplying a controlled flow of gas.

13. The unit of claim 1, wherein the pneumatic supply device of the pneumatic housing comprises a turbine for compressing the gas arriving in the pneumatic housing and for propelling the pressurised gas to the patient.

14. The unit of claim 1, wherein the pneumatic supply device of the pneumatic housing comprises a printed circuit board connected with sensors for sensing characteristics of the flow of gas within the pneumatic housing, the printed circuit board being further connected with the controller of the control housing for transmission of data characteristics of the flow of gas.

15. The unit of claim 14, wherein the sensors comprise a gas flow sensor and a pressure sensor.

16. The unit of claim 14, wherein the sensors comprise an oxygen sensor for sensing the amount of oxygen within the flow of gas.

17. The unit of claim 1, wherein the pneumatic housing comprises a gas outlet for being connected to gas conduit, the gas conduit being adapted for conveying the pressurised gas to the patient.

18. A gas supply unit for supplying pressurised gas to a patient comprising:
   a pneumatic housing including a pneumatic supply device for supplying a flow of gas to the patient,
   a control housing including a controller for controlling the flow of gas to be supplied to the patient, and
   a power supply housing for supplying power to the unit, wherein the three housings are distinct from one another and are designed for being removably coupled together to form a single unit;
   wherein the power supply housing comprises fasteners designed for preventing the pneumatic housing and the control housing from being uncoupled from one another as long as the power supply housing is coupled to the pneumatic housing and the control housing.

19. The unit of claim 18, wherein the fasteners comprise longitudinal grooves provided on the power supply housing for cooperation with longitudinal ridges provided on both the pneumatic housing and the control housing.

20. A respiratory system for supplying a patient breathing in successive cycles with pressurised gas, each cycle being defined by at least an inspiration phase and at least an expiration phase, said respiratory system comprising:
   a gas supply unit comprising a pneumatic housing including a pneumatic supply device for supplying a flow of gas to the patient, a control housing including a controller for controlling the flow of gas to be supplied to the patient, and a power supply housing for supplying power to the unit, wherein the three housings are distinct from one another and are designed for being removably coupled together to form a single unit, and wherein at least two of the pneumatic housing, the control housing and the power supply housing include complementary couplings configured for coupling the two housings to each other when aligned together;
   an expiratory valve, and
   gas conduit for conveying the pressurised gas from the gas supply unit to the patient through the expiratory valve, said expiratory valve being adapted for management of the gas flow depending on the phase of the cycle.

21. The system of claim 20, further comprising a connector for electrically connecting the controller of the control housing with the expiratory valve, and wherein the controller controls the expiratory valve in order to supply a controlled flow of gas to the patient from the expiratory valve.

* * * * *